(12) United States Patent
Afflitto

(10) Patent No.: US 10,016,259 B2
(45) Date of Patent: Jul. 10, 2018

(54) INCLINED ABUTMENT FOR A CEMENTED PROSTHESIS IN DENTAL IMPLANTOLOGY

(71) Applicant: Massimo Afflitto, Turin (IT)

(72) Inventor: Massimo Afflitto, Turin (IT)

(*) Notice: Subject to any disclaimer, the term of this patent is extended or adjusted under 35 U.S.C. 154(b) by 0 days.

(21) Appl. No.: 14/632,331

(22) Filed: Feb. 26, 2015

(65) Prior Publication Data

US 2015/0238285 A1 Aug. 27, 2015

(30) Foreign Application Priority Data

Feb. 27, 2014 (IT) ............... TO2014A0165
May 19, 2014 (IT) ............... TO2014A0395
Nov. 4, 2014 (IT) ............... TO2014A0911

(51) Int. Cl.
*A61C 8/00* (2006.01)

(52) U.S. Cl.
CPC ............ *A61C 8/0069* (2013.01); *A61C 8/006* (2013.01); *A61C 8/0056* (2013.01); *A61C 8/0066* (2013.01); *A61C 8/0068* (2013.01)

(58) Field of Classification Search
CPC ... A61C 8/0069; A61C 8/0056; A61C 8/0066; A61C 8/0068; A61C 8/006; A61C 8/0077; A61C 8/0001; A61C 3/14; A61C 8/005; A61C 8/0065; A61F 2/013
USPC .................................................. 433/201.1
See application file for complete search history.

(56) References Cited

U.S. PATENT DOCUMENTS

| | | | |
|---|---|---|---|
| 5,362,235 A * | 11/1994 | Daftary ............... | A61C 8/0048 433/172 |
| 5,779,480 A | 7/1998 | Groll et al. | |
| 6,540,722 B1 | 4/2003 | Boyle et al. | |
| 2005/0136378 A1 | 6/2005 | Ennajimi et al. | |
| 2006/0099549 A1 | 5/2006 | Engman | |
| 2010/0119993 A1 * | 5/2010 | Schulter ............... | A61C 8/0066 433/173 |

FOREIGN PATENT DOCUMENTS

| | | |
|---|---|---|
| WO | 2006/084346 A1 | 8/2006 |
| WO | 2012/156960 A1 | 11/2012 |

OTHER PUBLICATIONS

Unknown: "camlog® Esthomic® Abutments", 2011.
Unknown: "Product Catalog 2015 Straumann®", 2014.
Unknown: "LASAK Product catalog 2014/2015", 2014.

* cited by examiner

*Primary Examiner* — Ralph Lewis
(74) *Attorney, Agent, or Firm* — Jason D. Voight

(57) ABSTRACT

An inclined abutment for a cemented prosthesis in dental implantology. The abutment has a supragingival portion having a substantially truncated-cone shape with an elliptical base and having a longitudinal axis, an emergence surface coinciding with the elliptical base of the supragingival portion, and a transmucosal portion which has an elliptical base coinciding with the emergence surface and a longitudinal axis which ends at the apex with an antirotational connection for the insertion of the abutment in use. The volume of the supragingival portion remains essentially constant upon variation of the angle defined by the longitudinal axis of the supragingival portion and the longitudinal axis of the transmucosal portion, when the dimensions of the emergence surface and the height of the supragingival portion remain unchanged with respect to the longitudinal axis thereof.

15 Claims, 5 Drawing Sheets

INCLINED ABUTMENT FOR A CEMENTED PROSTHESIS IN DENTAL IMPLANTOLOGY

The present invention relates to an inclined abutment for a cemented prosthesis in dental implantology.

More in particular, the present invention relates to an abutment as specified, which has an essentially anatomical conformation.

BACKGROUND OF THE INVENTION

Dental implantology is a wide-spread technique of dental surgery, which allows to esthetically and functionally rehabilitate a patient suffering from total or partial edentulism by means of dental prostheses, consisting of devices (for example, in a metal material) surgically inserted in the mandible or maxilla bone, adapted for allowing the connection thereof relative to fixed or mobile prostheses for restoring the esthetic, masticatory and phonetic functions.

Different dental implantology surgery techniques, each characterised by different prosthesis implementation times and modes, are currently known in the state of the art.

By way of an example, three different types of prosthesis are:
  bone-level external hexagon;
  bone-level internal hexagon;
  transmucosal internal octagon.

Once said prosthesis is made, an abutment is secured relative thereto by means of a fixing screw.

Said abutment has an antirotation connecting portion relative to said prosthesis, usually showing a polygonal (preferably hexagonal or octagonal) cross-section, in order to minimise the risks of accidentally rotating the same.

More in particular, the abutments for cemented prosthesis have:
  a supragingival portion, usually, but not necessarily, provided with an abutment and/or bevels,
  an emergence surface, flat or undulated, from which said supragingival portion protrudes, and
  a transmucosal portion, opposite said supragingival portion with respect to said emergence surface, and which coronally ends with said emergence surface.

Said abutments may further be provided with a shoulder between said emergence surface and said supragingival portion.

Some examples of abutments according to the prior art are ESTOMIC ABUTMENT® CAMLOG®, STRAUMANN® ANATOMIC IPS E.MAX®1 ABUTMENT and LASAK ESTHETIC PLUS abutments for cemented protheses.

On the other hand, from document No. WO/2012/156960 an abutment showing a standard connecting device having hexagonal cross-section and an adjustable body is known, with said adjustable body being capable of being modified to obtain an inclined abutment having the desired spatial orientation by an angle comprised between +30° and −30°, and then connected with respect to the prosthesis.

Further types of abutments according to the prior art are described, for example, in document Nos. WO2006084346A1, US 20050136378A1, US 20060099549A1, WO01/52768A1, and U.S. Pat. No. 5,779,480 A.

The dental crown is then secured, by cementation, onto said supragingival portion of the abutment, with said crown being provided on the basis of on an impression made onto said one or more abutments, secured to said prosthesis.

Advantageously, said impression is made by means of telescopic/conometric caps in plastic or metal which, given the structure of said known abutments, cover the supragingival portion of the abutment by finger pressure.

Given the anatomical conformation of the dental arch, usually inclined abutments are used for better adapting the reconstructed tooth with respect to the anatomy of the oral cavity of the patient.

Said known abutments for a cemented prosthesis in dental implantology, however, have different orders of drawbacks.

Firstly, it is reported that said known abutments have a relatively small cementing surface, which results in the risk of a subsequent decementation or undesirable rotational phenomena of the artificial crown secured with respect to the same abutment.

The same drawbacks further result from said abutments not allowing, once the artificial crown has been cemented, the attainment of an advantageous distribution of the masticatory load from the artificial crown to the longitudinal axis of the prosthesis, thus further promoting the occurrence of decementation or undesirable rotation phenomena of the same crown.

Furthermore, said known abutments have such a structure which sometimes makes the insertion operations on the same of the artificial crown to be secured or the telescopic/conometric caps for detecting impressions impractical for the dentist.

On the other hand, the structure of said known abutments necessarily requires complex milling operations by the dental technician in order to make, in relation to each specific case, the abutment adapted with respect to the crown to be cemented on the same.

Starting from the notion of such drawbacks, the present invention aims to solve them.

BRIEF SUMMARY OF THE INVENTION

An object of the present invention is to provide an inclined abutment for a cemented prosthesis in dental implantology, which is capable of especially enhancing the seal of an artificial crown secured thereon by cementation, thus minimising the risk of any subsequent decementation or undesirable rotation of the same crown.

Furthermore, it is an object of the present invention to provide an inclined abutment as specified, which allows, once said artificial crown has been cemented thereon, attaining an optimum distribution of the masticatory load from the artificial crown to the longitudinal axis of the prosthesis, so as to further prevent risks of decementation or undesirable rotation of the same crown. It is also an object of the present invention to provide an inclined abutment as mentioned, which has a structure capable of making the insertion operations onto the same of the artificial crown to be secured or unified conometric caps for detecting impressions practical and safe for the dentist.

A further object of the present invention is to provide an inclined abutment as mentioned, which allows the dentist to make minimum and practical milling operations needed to make the same abutment adapted, in relation to each specific case, with respect to the crown to be cemented on the same.

In addition, it is an object of the present invention to provide an inclined abutment as specified which allows detecting an impression on the relative supragingival portion with a high degree of precision and in relatively short times.

On the other hand, it is an object of the present invention to provide an inclined abutment as specified, which has a relatively simple structure, easily made on an industrial scale and with relatively low costs.

In view of such objects, the present invention provides an inclined abutment for a cemented prosthesis in dental implantology, whose essential feature and further advantageous features are described herein.

More in particular, according to the present invention, said inclined abutment for a cemented prosthesis in dental implantology, comprising:
- a supragingival portion having a substantially truncated-cone shape with an elliptical base and having a longitudinal axis, hereinafter referred to as the longitudinal axis of the supragingival portion,
- an emergence surface coinciding with said elliptical base of said supragingival portion,
- a transmucosal portion which has an elliptical base coinciding with said emergence surface, a longitudinal axis hereinafter referred to as the longitudinal axis of the transmucosal portion and which ends at the apex with an antirotational connection for the insertion of said abutment in use, is characterised in that:
- said longitudinal axis of said supragingival portion and said longitudinal axis of said transmucosal portion form, relative to each other, a first angle, comprised between 5 and 35 degrees, which angle defines the inclination of the abutment in use, and
- the lateral surface of said supragingival portion forms with said longitudinal axis of said supragingival portion a second angle, comprised between 2 and 6 degrees, which angle defines the conometry of said supragingival portion, and in that
the volume of said supragingival portion remains essentially constant upon variation of said first angle of the abutment, when the dimensions of said emergence surface and the height of said supragingival portion remain unchanged with respect to said longitudinal axis of the same.

The present invention will become more apparent from the detailed description which follows, with reference to the drawing attached thereto, which is purely exemplary and therefore non-limiting.

DETAILED DESCRIPTION OF THE INVENTION

Figure 1:
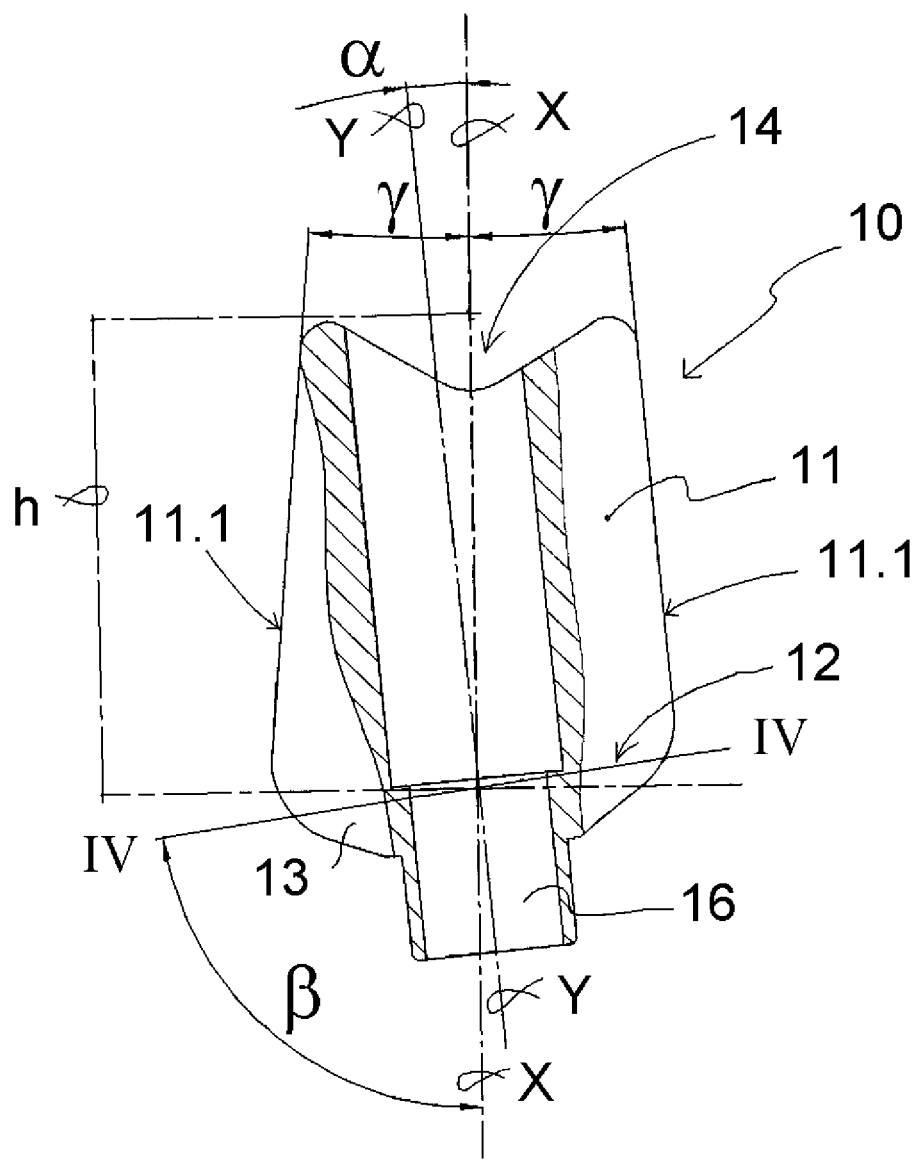
FIG. 1 is a schematic vertical sectional view of an inclined abutment for a cemented prosthesis in dental implantology according to a first modification the present exemplary embodiment of the invention.
Figure 2:
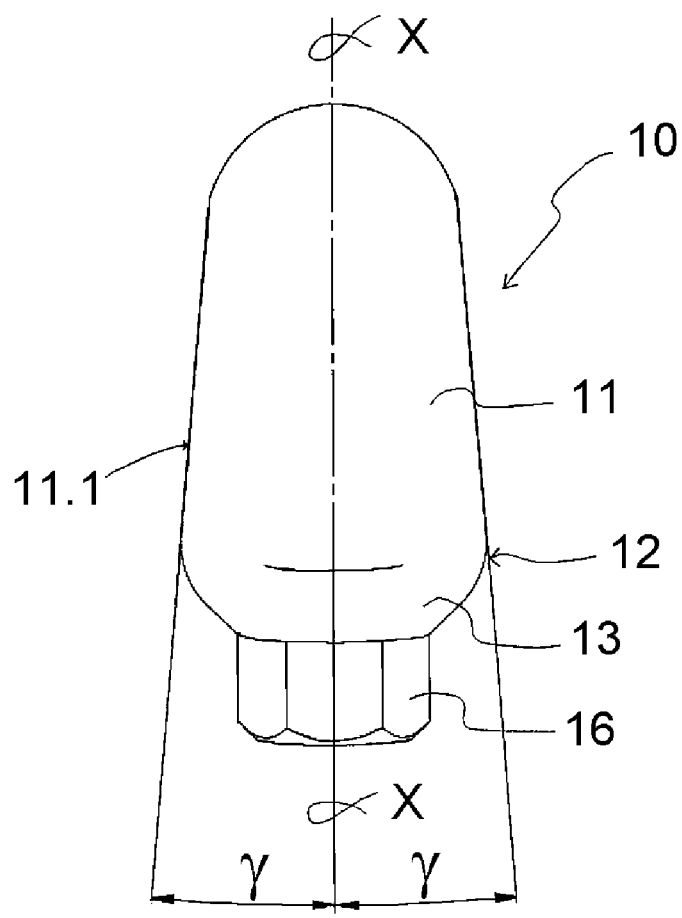
FIG. 2 is a schematic front elevation view of the abutment of FIG. 1.
Figure 3:
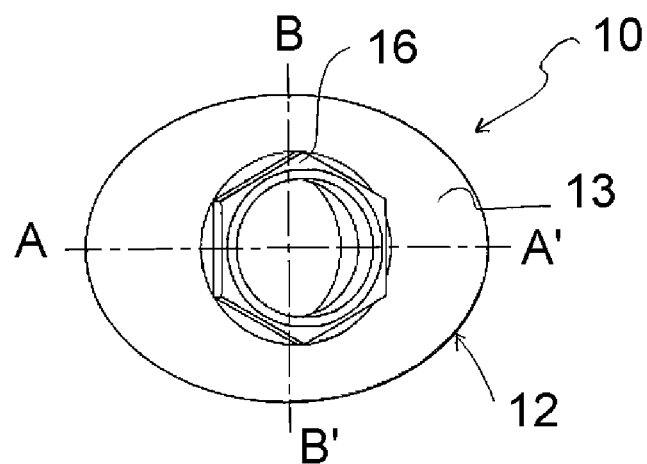
FIG. 3 is a schematic plan bottom view of the abutment of FIG. 1.
Figure 4:
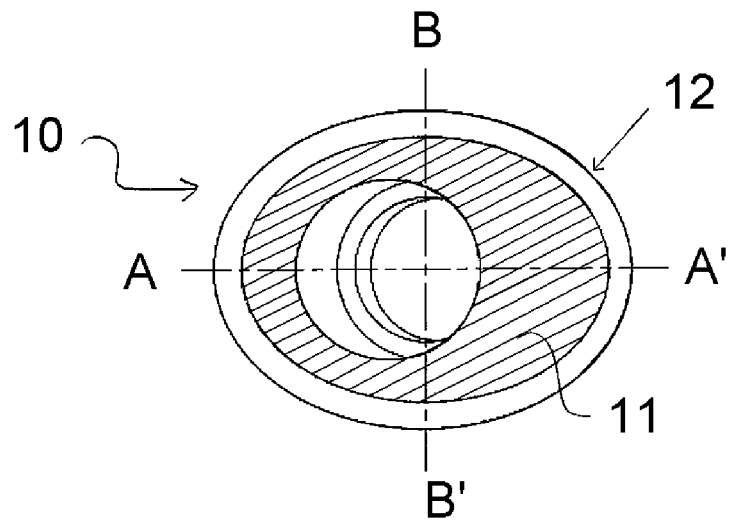
FIG. 4 is a sectional view according to the line IV-IV of FIG. 1.
Figure 5:
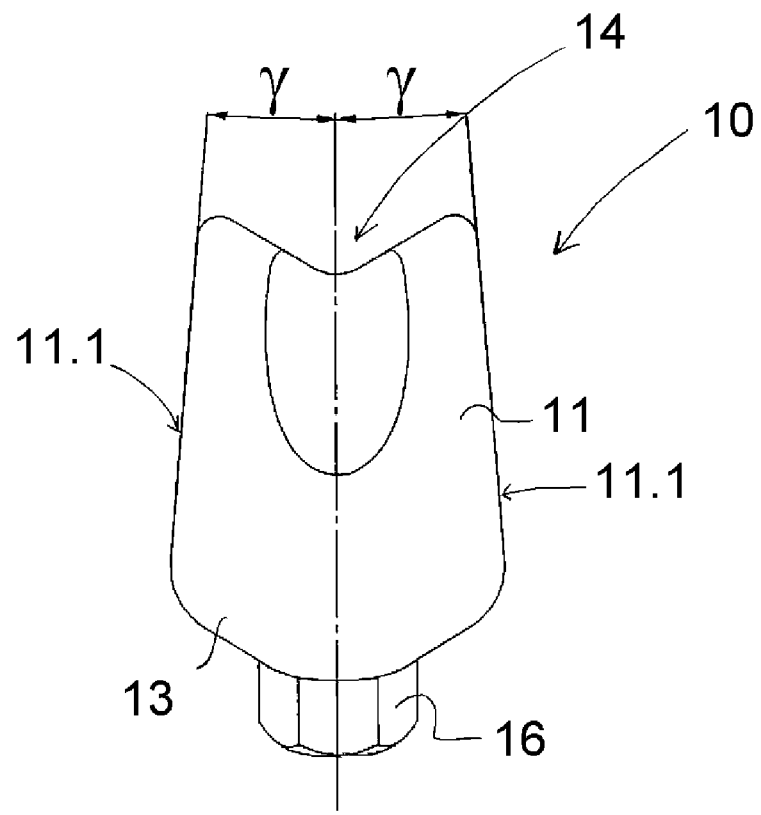
FIG. 5 is a schematic side elevation view of an inclined abutment for a cemented prosthesis in dental implantology according to a second modification of the present exemplary embodiment of the invention.

In the above-mentioned FIGS. 1 to 8, 10 indicates an inclined abutment for a cemented prosthesis in dental implantology according to an exemplary embodiment of the present invention.

Said inclined abutment 10 for a cemented prosthesis in dental implantology comprises according to the prior art:
- a supragingival portion 11 having a substantially truncated-cone shape with an elliptical base and having a longitudinal axis X-X, hereinafter referred to as the longitudinal axis of the supragingival portion 11,
- an emergence surface 12 coinciding with said elliptical base of said supragingival portion 11,
- a transmucosal portion 13 which has an elliptical base coinciding with said emergence surface 12, a longitudinal axis Y-Y hereinafter referred to as the longitudinal axis of the transmucosal portion 13 and which ends at the apex with an antirotational connection 16 for the insertion of said abutment 10 in use.

More in particular, according to the invention:
- said longitudinal axis X-X of said supragingival portion 11 and said longitudinal axis Y-Y of said transmucosal portion 13 form, relative to each other, a first angle $\alpha$; $\alpha'$, comprised between 5 and 35 degrees, which angle defines the inclination of the abutment 10 in use, and
- the lateral surface 11.1 of said supragingival portion 11 forms with said longitudinal axis X-X of said supragingival portion 11 a second angle $\gamma$, comprised between 2 and 6 degrees, which angle defines the conometry of said supragingival portion 11.

In addition, by virtue of the above-mentioned morphological features of the abutment 10, the volume of said supragingival portion 11 remains essentially constant upon variation of said first angle $\alpha$; $\alpha'$ of the abutment 10, when the dimensions of said emergence surface 12 and the height h of said supragingival portion 11 remain unchanged with respect to said longitudinal axis X-X of the same.

Advantageously, in the illustrated embodiment, said emergence surface 12 and said longitudinal axis X-X of said supragingival portion 11 form, relative to each other, a third angle $\beta$; $\beta'$, comprised between 75 and 90 degrees.

This significantly contributes to assisting the dentist in his/her operations, particularly when detecting an impression on said supragingival portion 11 of the abutment 10 by means of a unified conometric cap.

On the other hand, this equally contributes to giving greater stability to the abutment 10 and to the artificial crown (not shown) thereof once it has been placed in use on the same, optimising the antirotational effect as well as cooperating for the purposes of a better distribution of the masticatory load.

Hereinafter, for brevity, a plane passing by the longitudinal axis X-X of the supragingival portion 11 of the abutment 10 is referred to as the "longitudinal plane".

Advantageously, as is understood based on the illustrated embodiment (in particular, see FIGS. 1, 2, 5, 6), the upper base of said supragingival portion 11 has an essentially V-shaped recess 14 laying on the longitudinal plane which divides said supragingival portion 11 into two mirror-like halves passing through the major axis A-A' of said emergence surface 12; said essentially constant volume of said supragingival portion 11, comprising said V-shaped recess 14, substantially reproduces the volume of a natural tooth following a milling operation.

In this way, the overall cementation surface is increased, and the securing and subsequent seal of an artificial crown on said abutment 10 are greatly facilitated; any risks of accidental decementation or undesirable rotation of the artificial crown with respect to the abutment 10, once it has been cemented thereon, are therefore greatly reduced.

The above-mentioned advantageous effects are further enhanced by the fact that, as anticipated, the structure of the abutment 10 according to the present invention significantly facilitates the attainment of an optimum distribution of the masticatory load from the artificial crown to the longitudinal axis of the prosthesis.

Reference should be made, in particular, to the above-mentioned FIG. 1, which is a schematic vertical sectional view of an inclined abutment 10 for a cemented prosthesis in dental implantology, according to a first exemplary embodiment modification of the invention.

It should be noted that, as can be seen based on the above-mentioned drawing figure, said first and third angles $\alpha$, $\beta$ lay on a longitudinal plane which divides said abutment 10 into two mirror-like halves and contains the major axis A-A' of said emergence surface 12.

Advantageously, according to a first configuration of the present first embodiment modification of the invention:
- said emergence surface 12 has a major axis A-A' essentially of 6 mm and a minor axis B-B' essentially of 4.5 mm;
- said supragingival portion 11 has a height h essentially of 7 mm;
- said first angle $\alpha$ is essentially of 5 degrees;
- said third angle $\beta$ is essentially of 82 degrees; and
- said second angle $\gamma$ is essentially of 5 degrees.

Alternatively, according to a second possible advantageous configuration of the present first embodiment modification:
- said emergence surface 12 has a major axis A-A' essentially of 6 mm and a minor axis B-B' essentially of 4.5 mm;
- said supragingival portion 11 has a height h essentially of 7 mm;
- said first angle $\alpha$ is essentially of 17 degrees;
- said third angle $\beta$ is essentially of 82 degrees; and
- said second angle $\gamma$ is essentially of 5 degrees.

Likewise, according to a third configuration of the present first embodiment modification of the invention:
- said emergence surface 12 has a major axis A-A' essentially of 7 mm and a minor axis B-B' essentially of 5.2 mm;
- said supragingival portion 11 has a height h essentially of 8 mm;
- said first angle $\alpha$ is essentially of 7 degrees;
- said third angle $\beta$ is essentially of 82 degrees; and
- said second angle $\gamma$ is essentially of 6 degrees.

On the other hand, according to a fourth configuration of the present first embodiment modification of the present invention:
- said emergence surface 12 has a major axis A-A' essentially of 7 mm and a minor axis B-B' essentially of 5.2 mm;
- said supragingival portion 11 has a height h essentially of 8 mm;
- said first angle $\alpha$ is essentially of 15 degrees;
- said third angle $\beta$ is essentially of 82 degrees; and
- said second angle $\gamma$ is essentially of 6 degrees.

Clearly, it is understood that any further possible configurations of the present embodiment of said inclined abutment 10, provided that they are suitable for the intended use, are equally possible according to the invention.

Figure 6:
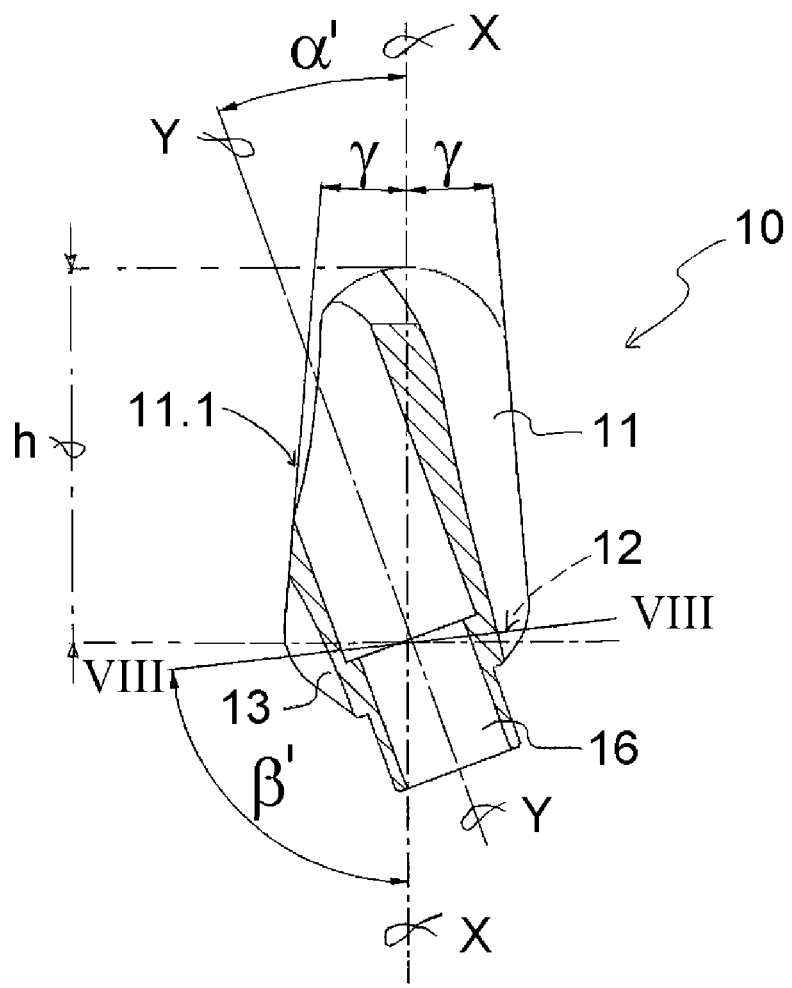
FIG. 6 is a schematic vertical sectional view of the abutment of FIG. 5.
Figure 7:
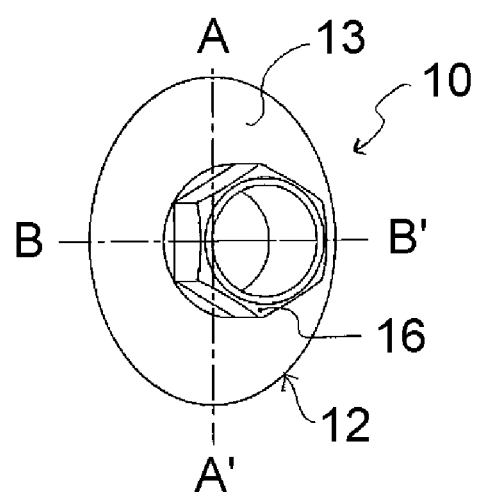
FIG. 7 is a schematic plan bottom view of the abutment of FIG. 5.
Figure 8:
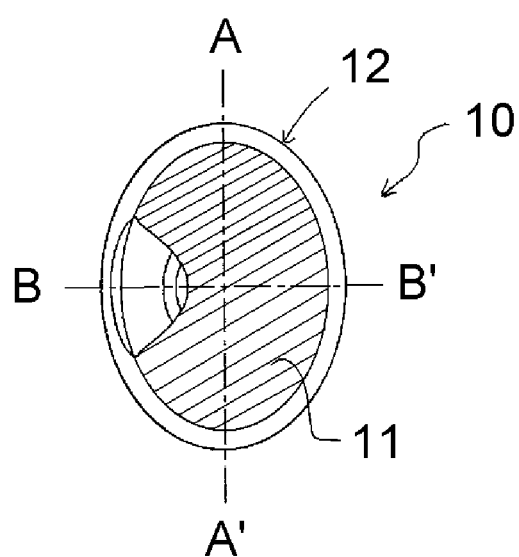
FIG. 8 is a sectional view according to the line VIII-VIII of FIG. 6.

Reference should be now made, in particular, to FIG. 6, which is a schematic vertical sectional view of an inclined abutment 10 for a cemented prosthesis in dental implantology, according to a second exemplary embodiment modification of the invention, wherein the numbering of similar parts is kept unchanged as specified with reference to the first embodiment modification.

In the illustrated embodiment modification, said first and third angles $\alpha'$, $\beta'$ lay on a longitudinal plane which divides said abutment 10 into two mirror-like halves and contains the minor axis B-B' of said emergence surface 12.

Advantageously, according to a first configuration of the present second embodiment modification of the invention:
- said emergence surface 12 has a major axis A-A' essentially of 6 mm and a minor axis B-B' essentially of 4.5 mm;
- said supragingival portion 11 has a height h essentially of 7 mm;
- said first angle $\alpha'$ is essentially of 20 degrees;
- said third angle $\beta'$ is essentially of 82 degrees; and
- said second angle $\gamma$ is essentially of 5 degrees.

Alternatively, according to a second possible advantageous configuration of the present second embodiment modification:
- said emergence surface 12 has a major axis A-A' essentially of 7 mm and a minor axis B-B' essentially of 5.2 mm;
- said supragingival portion 11 has a height h essentially of 8 mm;
- said first angle $\alpha'$ is essentially of 20 degrees;
- said third angle $\beta'$ is essentially of 82 degrees; and
- said second angle $\gamma$ is essentially of 6 degrees.

Likewise, according to a third configuration of the present second embodiment modification of the invention:
- said emergence surface 12 has a major axis A-A' essentially of 5.2 mm and a minor axis B-B' essentially of 4.2 mm;
- said supragingival portion 11 has a height h essentially of 9 mm;
- said first angle $\alpha'$ is essentially of 6 degrees;
- said third angle $\beta'$ is essentially of 82 degrees; and
- said second angle $\gamma$ is essentially of 4 degrees.

On the other hand, according to a fourth configuration of the present second embodiment modification of the present invention:
- said emergence surface 12 has a major axis A-A' essentially of 5.2 mm and a minor axis B-B' essentially of 4.2 mm;
- said supragingival portion 11 has a height h essentially of 9 mm;
- said first angle $\alpha'$ is essentially of 14 degrees;
- said third angle $\beta'$ is essentially of 82 degrees; and
- said second angle $\gamma$ is essentially of 4 degrees.

Clearly, it is understood that any further possible configurations of the present embodiment of said inclined abutment 10, provided that they are suitable for the intended use, are equally possible according to the invention.

Advantageously, said supragingival portion 11 of the abutment 10 is provided in use according to an arrangement which allows detecting the position of said same supragingival portion 11, as well as said antirotational connection 16, by means of a unified conometric cap.

This allows to significantly assist the dentist in the operation of detecting the impression on the abutment 10, as well as to greatly increase the precision of the same impression, obtaining at the same time a significant reduction of the times needed for the intended purpose.

As can be seen based on the foregoing, said inclined abutment 10 for a cemented prosthesis in dental implantology especially enhances the seal of an artificial crown secured thereon by cementation, thus minimising the risk of any subsequent decementation or undesirable rotation of the same crown.

Furthermore, said inclined abutment 10 as specified allows, once said artificial crown has been cemented thereon, attaining an optimum distribution of the masticatory load, so as to further prevent risks of decementation or undesirable rotation of the same crown.

In addition, said inclined abutment 10 as mentioned has a structure capable of making the insertion operations on the same of the artificial crown to be secured or unified conometric caps for detecting impressions practical and safe for the dentist.

Moreover, said inclined abutment 10 as mentioned allows the dentist to make minimum and practical milling operations needed to make the same abutment adapted, in relation to each specific case, with respect to the crown to be cemented on the same.

In addition, said inclined abutment 10 as specified allows detecting an impression on the relative supragingival portion with a high degree of precision and in relatively short times.

On the other hand, said inclined abutment 10 as specified has a relatively simple structure, easily made on an industrial scale and with relatively low costs.

As it appears from the above description, the present invention allows the objects described in the introduction to be achieved in a simple and advantageous manner.

The invention claimed is:

1. An inclined abutment (10) for a cemented prosthesis in dental implantology, comprising:
    a supragingival portion (11) having a substantially truncated-cone shape with an elliptical base and having a longitudinal axis (X-X), hereinafter referred to as the longitudinal axis of the supragingival portion (11),
    an emergence surface (12) coinciding with said elliptical base of said supragingival portion (11), said emergence surface (12) having a major axis (A-A') and a minor axis (B-B'),
    a transmucosal portion (13) which has an elliptical base coinciding with said emergence surface (12), a longitudinal axis (Y-Y) hereinafter referred to as the longitudinal axis of the transmucosal portion (13) and which ends at an apex with an antirotational connection (16) for the insertion of said abutment (10) in use,
characterised in that:
    said longitudinal axis (X-X) of said supragingival portion (11) and said longitudinal axis (Y-Y) of said transmucosal portion (13) form, relative to each other, a first angle (α; α'), comprised between 5 and 35 degrees, which angle defines the inclination of the abutment (10) in use,
    the lateral surface (11.1) of said supragingival portion (11) forms with said longitudinal axis (X-X) of said supragingival portion (11) a second angle (γ), comprised between 2 and 6 degrees, which angle defines the conometry of said supragingival portion (11), and
    said emergence surface (12) and said longitudinal axis (X-X) of said supragingival portion (11) form, relative to each other, a third angle (β; β'), comprised between 75 and 90 degrees,
    wherein said first angle (α; α') and said third angle (β; β') lay on a longitudinal plane which divides said abutment into two mirror-like halves,
and in that
a volume of said supragingival portion (11) remains essentially constant upon variation of said first angle (α; α') of the abutment (10), when the dimensions of said emergence surface (12) and a height (h) of said supragingival portion (11) and said third angle (β; β') of said emergence surface (12) with respect to said longitudinal axis (X-X) of the same remain unchanged.

2. An inclined abutment (10) according to claim 1, characterised in that
    an upper base of said supragingival portion (11) has an essentially V-shaped recess (14) laying on the longitudinal plane which divides said supragingival portion (11) into two mirror-like halves, said longitudinal plane passing through the major axis (A-A') of said emergence surface (12) and said longitudinal axis (X-X) of said supragingival portion (11),
    wherein said recess (14) lays on the longitudinal plane such that each of the two mirror-like halves has a recess portion which is also V-shaped,
    and in that
    said essentially constant volume of said supragingival portion (11), with said V-shaped recess (14) being comprised, substantially reproduces the volume of the natural tooth following a milling operation.

3. An inclined abutment (10) according to claim 1, characterised in that
    said longitudinal plane which divides said abutment (10) into two mirror-like halves contains the major axis (A-A') of said emergence surface (12) and said longitudinal axis (X-X) of said supragingival portion (11),
    and in that:
        said emergence surface (12) has a major axis (A-A') of 6 mm and a minor axis (B-B') of 4.5 mm;
        said supragingival portion (11) has a height (h) of 7 mm;
        said first angle (α) is of 5 degrees;
        said third angle (β) is of 82 degrees; and
        said second angle (γ) is of 5 degrees.

4. An inclined abutment (10) according to claim 1, characterised in that
    said longitudinal plane which divides said abutment (10) into two mirror-like halves contains the major axis (A-A') of said emergence surface (12) and said longitudinal axis (X-X) of said supragingival portion (11),
    and in that:
        said emergence surface (12) has a major axis (A-A') of 6 mm and a minor axis (B-B') essentially of 4.5 mm;
        said supragingival portion (11) has a height (h) of 7 mm;
        said first angle (α) is of 17 degrees;
        said third angle (β) is of 82 degrees; and
        said second angle (γ) is of 5 degrees.

5. An inclined abutment (10) according to claim 1, characterised in that
    said longitudinal plane which divides said abutment (10) into two mirror-like halves contains the major axis (A-A') of said emergence surface (12) and said longitudinal axis (X-X) of said supragingival portion (11),
    and in that:
        said emergence surface (12) has a major axis (A-A') of 7 mm and a minor axis (B-B') of 5.2 mm;
        said supragingival portion (11) has a height (h) essentially of 8 mm;

said first angle (α) is of 7 degrees;
said third angle (β) is of 82 degrees; and
said second angle (γ) is of 6 degrees.

6. An inclined abutment (10) according to claim 1, characterised in that
said longitudinal plane which divides said abutment (10) into two mirror-like halves contains the major axis (A-A') of said emergence surface (12) and said longitudinal axis (X-X) of said supragingival portion (11), and in that:
said emergence surface (12) has a major axis (A-A') of 7 mm and a minor axis (B-B') of 5.2 mm;
said supragingival portion (11) has a height (h) of 8 mm;
said first angle (α) is of 15 degrees;
said third angle (β) is of 82 degrees; and
said second angle (γ) is of 6 degrees.

7. An inclined abutment (10) according to claim 1, characterised in that
said longitudinal plane which divides said abutment (10) into two mirror-like halves contains the minor axis (B-B') of said emergence surface (12) and said longitudinal axis (X-X) of said supragingival portion (11), and in that:
said emergence surface (12) has a major axis (A-A') of 6 mm and a minor axis (B-B') of 4.5 mm;
said supragingival portion (11) has a height (h) essentially of 7 mm;
said first angle (α') is of 20 degrees;
said third angle (β') is of 82 degrees; and
said second angle (γ) is of 5 degrees.

8. An inclined abutment (10) according to claim 1, characterised in that
said longitudinal plane which divides said abutment (10) into two mirror-like halves contains the minor axis (B-B') of said emergence surface (12) and said longitudinal axis (X-X) of said supragingival portion (11), and in that:
said emergence surface (12) has a major axis (A-A') essentially of 7 mm and a minor axis (B-B') of 5.2 mm;
said supragingival portion (11) has a height (h) of 8 mm;
said first angle (α') is of 20 degrees;
said third angle (β') is of 82 degrees; and
said second angle (γ) is of 6 degrees.

9. An inclined abutment (10) according to claim 1, characterised in that
said longitudinal plane which divides said abutment (10) into two mirror-like halves contains the minor axis (B-B') of said emergence surface (12) and said longitudinal axis (X-X) of said supragingival portion (11), and in that:
said emergence surface (12) has a major axis (A-A') of 5.2 mm and a minor axis (B-B') of 4.2 mm;
said supragingival portion (11) has a height (h) of 9 mm;
said first angle (α') is of 6 degrees;
said third angle (β') is of 82 degrees; and
said second angle (γ) is of 4 degrees.

10. An inclined abutment (10) according to claim 1, characterised in that
said longitudinal plane which divides said abutment (10) into two mirror-like halves contains the minor axis (B-B') of said emergence surface (12) and said longitudinal axis (X-X) of said supragingival portion (11), and in that:
said emergence surface (12) has a major axis (A-A') of 5.2 mm and a minor axis (B-B') of 4.2 mm;
said supragingival portion (11) has a height (h) of 9 mm;
said first angle (α') is of 14 degrees;
said third angle (β') is of 82 degrees; and
said second angle (γ) is of 4 degrees.

11. An inclined abutment (10) according to claim 1, characterised in that said supragingival portion (11) is provided in use according to an arrangement which allows detecting the position of said same supragingival portion (11), as well as said antirotational connection (16), by means of a unified conometric cap.

12. An inclined abutment (10) according to claim 1, wherein said antirotational connection (16) has a form of a hexagon, the longitudinal plane contains the major axis (A-A') of said emergence surface (12) and said longitudinal axis (X-X) of said supragingival portion (11), and said longitudinal plane divides the antirotational connection (16) at midpoints of sides of the hexagon rather than at vertices thereof.

13. An inclined abutment (10) according to claim 1, which consists of a single piece and does not have a shoulder at the emergence surface (12).

14. An inclined abutment (10) according to claim 1, wherein the second angle (γ) also lays on the longitudinal plane and the second angle (γ) is maintained over the majority of the height (h) of the supragingival portion on both sides of the longitudinal axis of the supragingival portion.

15. An inclined abutment (10) according to claim 1, wherein the antirotational connection (16) shares the longitudinal axis (Y-Y) of the transmucosal portion.

* * * * *